US00PP32457P2

(12) United States Plant Patent
Olesen

(10) Patent No.: US PP32,457 P2
(45) Date of Patent: Nov. 17, 2020

(54) HYBRID TEA ROSE PLANT NAMED 'POULREN028'

(50) Latin Name: ***Rosa* hybrid**
Varietal Denomination: Poulren028

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/602,239

(22) Filed: Sep. 4, 2019

(51) Int. Cl.
*A01H 6/74* (2018.01)
*A01H 5/02* (2018.01)

(52) U.S. Cl.
USPC ..... Plt./138

(58) Field of Classification Search
USPC ..... Plt./138
CPC ..... A01H 5/02; A01H 6/74
See application file for complete search history.

(56) References Cited

PUBLICATIONS www.poulsenroser.AK/de/roses/ShowProduct/33269?productGroup=REN.2020.*
PLUTO Plant Variety Database Mar. 6, 2020. p. 1.*

* cited by examiner

*Primary Examiner* — Annette H Para

(57) ABSTRACT

A new garden rose plant of the Hybrid Tea class which has abundant, deep pink flowers and attractive foliage. This new and distinct variety has shown to be uniform and stable in the resulting generations from asexual propagation.

2 Drawing Sheets

Botanical designation: *Rosa* hybrid.
Variety denomination: 'Poulren028'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2007 and the resulting seeds were planted in a controlled environment in Fredensborg, Denmark. The new variety, named 'Poulren028', originated as a single seedling from the stated cross.

The new variety may be distinguished from its male pollen parent and female seed parent primarily by the following characteristics. The male pollen parent plant has orange yellow flowers while the new variety has deep pink flowers. The female seed parent plant has red flowers while the new variety has deep pink flowers.

The objective of the hybridization of this rose variety was to create a new and distinct variety with unique qualities, such as:

1. Uniform and abundant deep pink flowers;
2. Vigorous, but compact growth when propagated on its own roots;
3. Exceptional disease resistance; and
4. Perfumed flowers.

This combination of qualities is not present in previously available commercial cultivars of this type, known to the inventor, and distinguish 'Poulren028' from all other varieties of which we are aware.

As part of the rose development program, Mogens N. Olesen germinated the seeds from the aforementioned hybridization during winter of 2007 and conducted evaluations on the resulting seedlings in a controlled environment in Fredensborg, Denmark. 'Poulren028' was selected in the spring of 2008 by the inventor as a single plant from the progeny of the aforementioned hybridization.

Asexual reproduction of 'Poulren028' by rooted cuttings was first done by Mogens N. Olesen in the nursery in Fredensborg, Denmark in July, 2008. This initial and other subsequent asexual propagations conducted in controlled environments have demonstrated that the characteristics of 'Poulren028' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulren028'.

Specifically illustrated in FIG. 1 of the drawings are open flowers viewed from above and the side, flower petals detached, sepals detached revealing reproductive flower parts.

Figure 1:
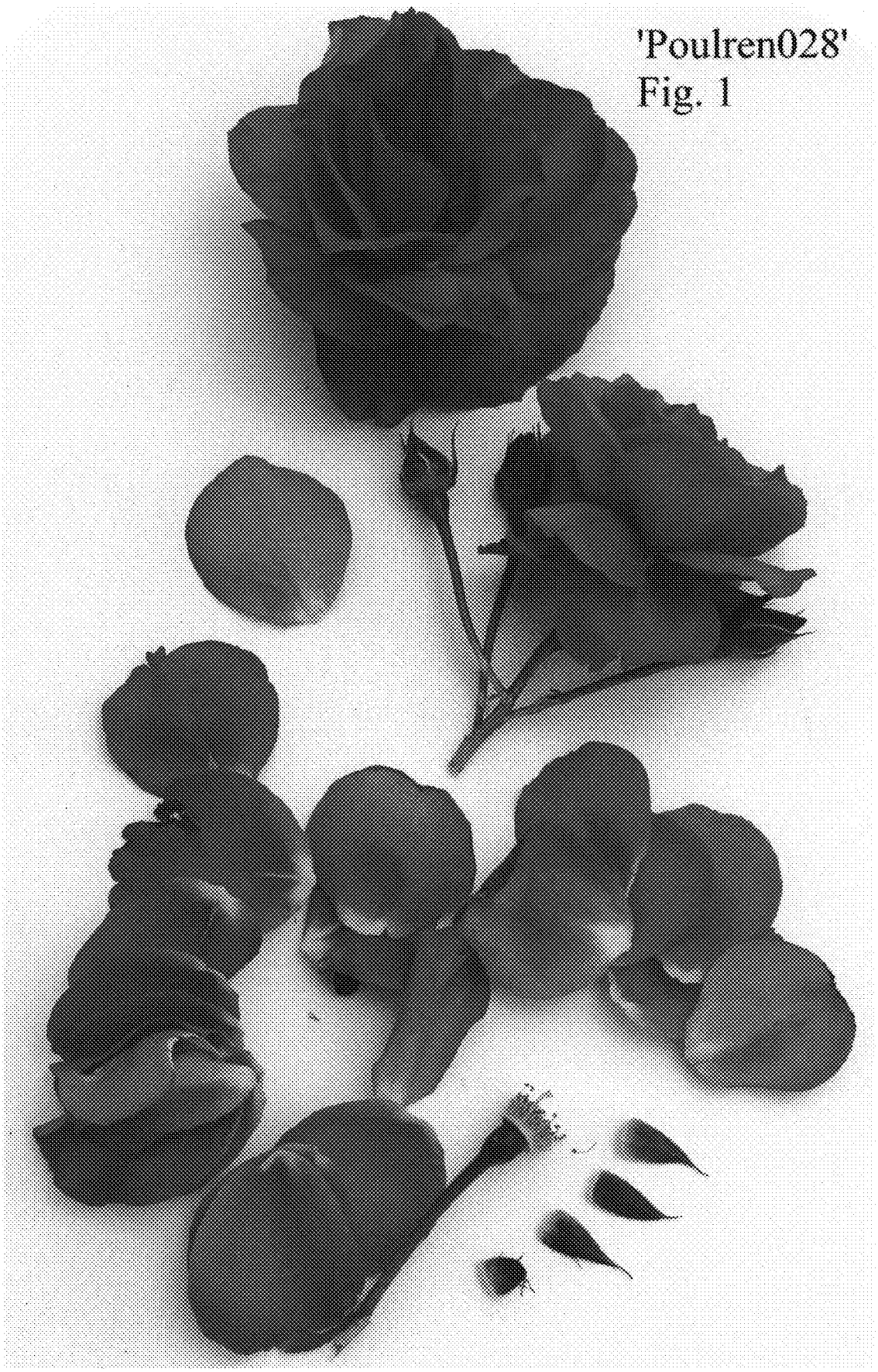
Figure 2:
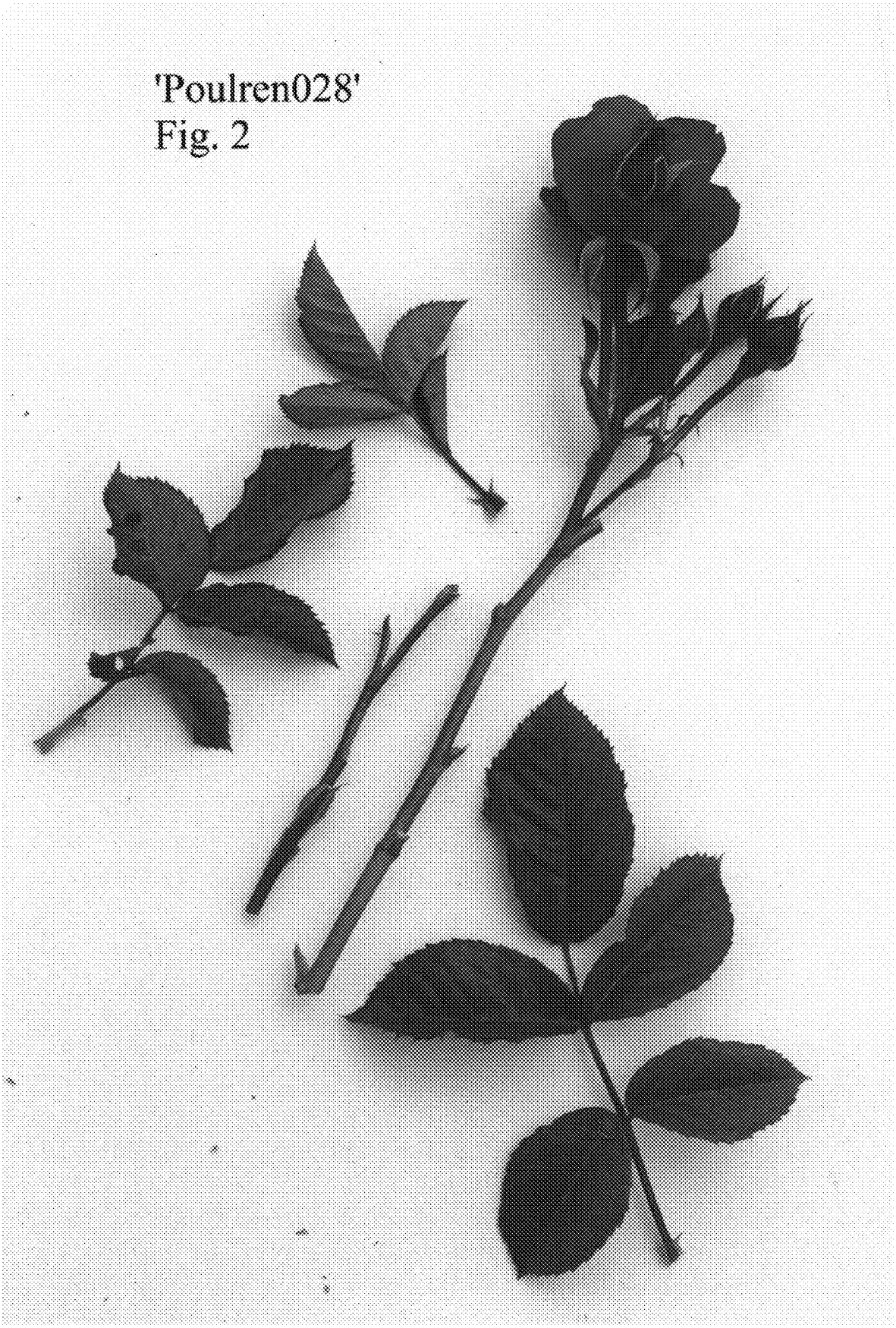

Specifically illustrated in FIG. 2 of the drawings are bare stems, mature and juvenile leaves, and a cluster of flowers on the branch. Plants shown are 2 years of age.

DETAILED DESCRIPTION OF THE VARIETY

The following is a description of 'Poulren028', as observed in its growth in a field nursery in Linn County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulren021', U.S. Plant Pat. No. 26,165 are compared to 'Poulren028' in Chart 1.

CHART 1

| | 'Poulren028' | 'Poulren021' |
|---|---|---|
| Petal Count | 25 petals | 60 petals |
| Flower Diameter | 90 to 120 mm | 100 mm |
| General Tonality of Flower Color | Red-Purple Group 60B | Red-Purple Group 61C |

FLOWER AND FLOWER BUD

Blooming habit: Continuous.

Flower bud:

*Size.*—Upon opening, 35 mm in length from base of receptacle to end of bud. Bud diameter is 18 mm.

*Bud form.*—Ovoid, broad at the base.

*Bud color.*—As sepals divide petals are Greyed- Purple Group N186C.

*Sepal inner surface.*—Color: Yellow-Green Group 146D with strong intonations of Greyed-Purple Group 183A and Greyed-Purple Group N186C. Surface: Lightly pubescent.

*Sepal outer surface.*—Color: Yellow-Green Group 144A with strong intonations of Greyed-Purple Group 183A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—32 mm long, 11 mm wide.

*Receptacle.*—Texture: Smooth. Size: 9 mm in height, 9 mm wide. Color: Yellow-Green Group 144A with strong intonations of Greyed-Purple Group 183A. Shape: Campanulate.

*Pedicel.*—Surface: Smooth. Length: 52 mm. Diameter: 4 mm on average. Color: Yellow-Green Group 144A with intonations of Greyed-Purple Group 183B. Strength: Strong.

*Peduncle.*—Length: 2 to 9 cm. Diameter: About mm. Color: Yellow-Green Group 144A with intonations of Greyed-Purple Group 183B. Texture: Smooth.

Flower bud development: Flower buds are borne in clusters of 5 to 15 flower buds per stem. Flower bloom.

*Fragrance.*—Strong perfume.

*Duration.*—The blooms have a duration on the plant of approximately 10 days. Petals fall cleanly away from plant after flowers have fully matured.

*Size.*—Flower diameter is 90 to 120 mm when open. Flower depth is 50 to 60 mm.

*Flower shape.*—High centered, double, with a high pointed center which is initially tightly closed, then turning into an open cup after fully mature.

*Shape of flower, side view.*—The upper portion is flat. The lower portion is concave.

Petalage: Under normal conditions, flowers have about 25 petals.

General tonality of flower: Open flowers are Red-Purple Group 60B.

Petal color:

*Upon opening, outer and inner petals.*—Upper surface: Red-Purple Group 60B. Lower surface: Red-Purple Group 60C with occasional streaks Yellow Group 4C.

*Basal petal spots, upon opening.*—Upper surface: Yellow Group 6B. Lower surface: Yellow Group 4B.

*After opening, petals.*—Upper surface: Red-Purple Group 60B. Lower surface: Red-Purple Group 60C with occasional streaks Yellow Group 4C

*Basal petal spots, after opening.*—Upper surface: Yellow Group 6B. Lower surface: Yellow Group 4B.

Petals:

*Petal reflex.*—Slightly reflexed.

*Margin.*—Entire and uniform. Moderate undulations.

*Shape.*—Broad and elliptic. Apex shape: Rounded. Base shape: Acute.

*Size.*—60 mm (l)×60 mm (w).

*Texture.*—Smooth.

*Thickness.*—Average.

Petaloids:

*Size.*—15 mm (l) by 9 mm (w).

*Quantity.*—About 3.

*Shape.*—Elliptical with an acute base and rounded apices.

*Color.*—Red-Purple Group 60B with a petaloid spot of Yellow Group 6B on the upper surface, Red-Purple Group 60C on the undersurface, with a spot of Yellow Group 4B.

Reproductive flower parts:

*Pollen.*—None observed.

*Anthers.*—Size: 2 mm in length. Color: Yellow Group 11C. Quantity: 55 on average.

*Filaments.*—Color: Yellow Group 10A. Length: 6 mm.

*Pistils.*—Length: 6 mm. Quantity: on average.

*Stigmas.*—Color: Green-White Group 157A.

*Styles.*—Color: Green-White Group 157A.

*Location of stigmas.*—Inferior in location relative to the length of the filaments and the height of the anthers.

*Hips.*—None Observed.

PLANT

Plant growth: Upright. Plants are 110 to 120 cm in height, and 95 cm wide.

Stems:

*Color of juvenile growth.*—Yellow-Green Group 144A with shades of Greyed-Purple Group 183B.

*Color of mature growth.*—Yellow-Green Group 146C with shades of Greyed-Purple Group 183B.

*Length.*—Canes are about 30 to 60 cm from the base of the plant to the flowering portion.

*Diameter.*—About 8 mm.

*Internodes.*—On mature canes about 75 mm between nodes.

*Surface texture.*—Young wood: Smooth. Older wood: Smooth.

Long prickles: None observed.

Plant foliage:

*Compound leaf.*—175 mm (l)×120 (w).

*Quantity.*—2 leaves per 10 cm of stem on average.

*Leaf bearing angle to the stem.*—45 degrees.

*Color of juvenile foliage*.—Upper side: Yellow-Green Group 144A with intonations of Greyed-Purple Group 183B at margins. Lower side: Yellow-Green Group 144B.

*Color of mature foliage*.—Upper side: Yellow-Green Group 147A. Lower side: Yellow-Green Group 147B.

Plant leaves and leaflets:

*Stipules*.—Size: 22 mm long, 3 mm wide. Quantity: 2 per compound leaf. Shape: Linear, slightly broad based with outward extending apices. Margins: Finely serrated. Color:

*Petiole*.—Length: About 55 mm. Diameter: 2 mm. Upper surface color: Greyed-Purple Group 183B at margins. Lower surface color: Yellow-Green Group 144A.

*Rachis*.—Length: About 55 mm. Upper surface color: Greyed-Purple Group 183B at margins. Lower surface color: Yellow-Green Group 144A.

*Leaflet*.—Quantity: Normally 5 leaflets. Margins: Serrated. Size: Terminal leaflets are about 80 mm long, 48 mm wide. Shape: Generally elliptical. Base: Rounded. Apex: Mucronate. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

We claim:

1. A new and distinct variety of rose plant of the Hybrid Tea rose class named 'Poulren028', substantially as illustrated and described herein, due to its abundant deep pink flowers, disease resistance, and extended period of bloom.

* * * * *

'Poulren028'

'Poulren028'